United States Patent [19]

Schrimpf

[11] Patent Number: 5,752,919
[45] Date of Patent: May 19, 1998

[54] MITIGATION OF RESPIRATORY ARTIFACT IN BLOOD PRESSURE SIGNAL USING LINE SEGMENT SMOOTHING

[75] Inventor: Kathleen Schrimpf, New Port Richey, Fla.

[73] Assignee: Johnson & Johnson Medical, Inc., New Brunswick, N.J.

[21] Appl. No.: 768,276

[22] Filed: Dec. 17, 1996

[51] Int. Cl.$^6$ .................................................. A61B 5/00
[52] U.S. Cl. ........................................ 600/493; 600/494
[58] Field of Search ........................ 600/450, 493–497, 600/561

[56] References Cited

U.S. PATENT DOCUMENTS

| | | | |
|---|---|---|---|
| 3,536,062 | 10/1970 | Horn | 128/2.05 |
| 3,791,378 | 2/1974 | Hochberg et al. | 128/2.05 |
| 3,885,551 | 5/1975 | Massie | 128/2.05 |
| 4,140,110 | 2/1979 | Jansen et al. | 128/2.05 |
| 4,190,886 | 2/1980 | Sherman | 364/415 |
| 4,223,681 | 9/1980 | Sherman | 128/672 |
| 4,331,156 | 5/1982 | Apple et al. | 128/688 |
| 4,349,034 | 9/1982 | Ramsey, III | 128/681 |
| 4,360,029 | 11/1982 | Ramsey, III | 128/681 |
| 4,367,751 | 1/1983 | Link et al. | 128/682 |
| 4,408,614 | 10/1983 | Weaver et al. | 128/680 |
| 4,409,986 | 10/1983 | Apple et al. | 128/715 |
| 4,667,680 | 5/1987 | Ellis | 128/672 |
| 4,777,959 | 10/1988 | Wallach et al. | 128/677 |
| 4,785,820 | 11/1988 | Brooks | 128/681 |
| 4,860,759 | 8/1989 | Kahn et al. | 128/668 |
| 4,870,973 | 10/1989 | Ueno | 128/680 |
| 4,889,133 | 12/1989 | Nelson et al. | 128/681 |
| 4,917,098 | 4/1990 | Murase | 600/494 |
| 4,924,874 | 5/1990 | Murase | 600/494 |
| 4,949,710 | 8/1990 | Dorsett et al. | 128/680 |
| 4,974,597 | 12/1990 | Walloch | 128/680 |
| 5,005,581 | 4/1991 | Honeyager | 128/681 |
| 5,014,714 | 5/1991 | Millay et al. | 128/672 |
| 5,094,244 | 3/1992 | Callahan et al. | 128/67 |
| 5,111,826 | 5/1992 | Nasiff | 128/672 |
| 5,140,991 | 8/1992 | Niwa | 128/687 |
| 5,152,296 | 10/1992 | Simons | 128/670 |
| 5,181,517 | 1/1993 | Hickey | 128/673 |
| 5,199,438 | 4/1993 | Pearlman | 128/670 |
| 5,224,484 | 7/1993 | Newell | 128/670 |
| 5,243,992 | 9/1993 | Eckerle et al. | 128/690 |
| 5,253,648 | 10/1993 | Walloch | 128/681 |
| 5,337,750 | 8/1994 | Walloch | 128/680 |
| 5,343,868 | 9/1994 | Kurscheidt et al. | 128/673 |
| 5,577,508 | 11/1996 | Medero | 600/494 |
| 5,584,299 | 12/1996 | Sakai et al. | 600/493 |

FOREIGN PATENT DOCUMENTS

| | | |
|---|---|---|
| 274729 | 7/1988 | European Pat. Off. . |
| 536782 | 4/1993 | European Pat. Off. . |
| 563425 | 10/1993 | European Pat. Off. . |
| 581313 | 2/1994 | European Pat. Off. . |
| WO 92/03966 | 3/1992 | WIPO . |

OTHER PUBLICATIONS

Article entitled "Interpretation of Beat-To-Beat Blood Pressure Values in the Presence of Ventilatory Changes," by David M. Ellis, *Journal of Clinical Monitoring*, vol. 1, No. 1, Jan. 1985, pp. 65–70.

*Primary Examiner*—Robert L. Nasser
*Attorney, Agent, or Firm*—Woodcock Washburn Kurtz Mackiewicz & Norris LLP

[57] ABSTRACT

A blood pressure monitoring apparatus which reduces the effects of respiration artifacts in the blood pressure samples prior to display by determining, for each heart beat detected in the blood pressure samples, the blood pressure at a median point of a line connecting a systolic, diastolic, or mean value for a current heart beat with a corresponding systolic, diastolic, or mean value for a heart beat N-1 heart beats prior to the current heart beat. The median blood pressure value for the current heart beat is then averaged with the blood pressure values of the median points of numerous previous heart beats to the current heart beat, and the resulting average is output to the display as indicative of the systolic, diastolic, or mean pressure for the current heart beat. This process is repeated for each heart beat, as desired, until the systolic, diastolic, and mean pressures are determined for each heart beat. The method is advantageous in that it favors stable parts of the blood pressure waveform (end expiratory portions) yet actively smooths the variable parts of the blood pressure waveform.

18 Claims, 4 Drawing Sheets

BEAT PROCESSOR 18

RESPIRATORY ARTIFACT ALGORITHM

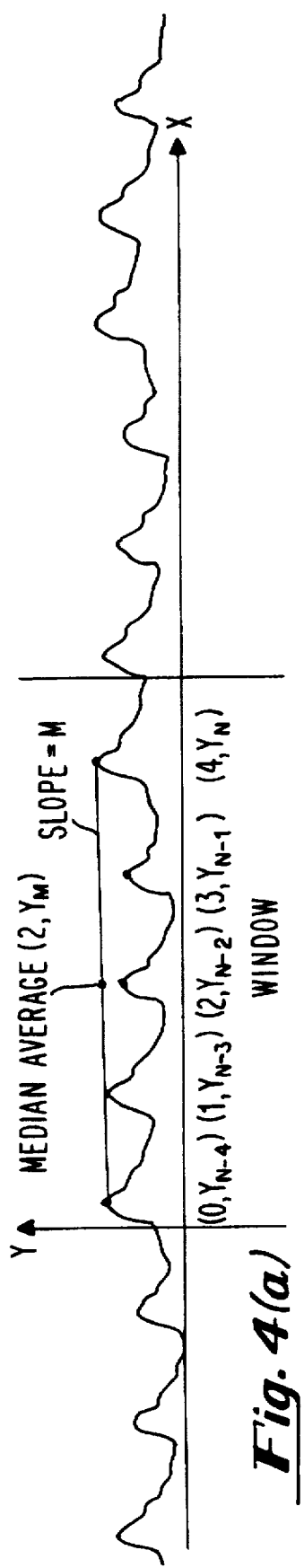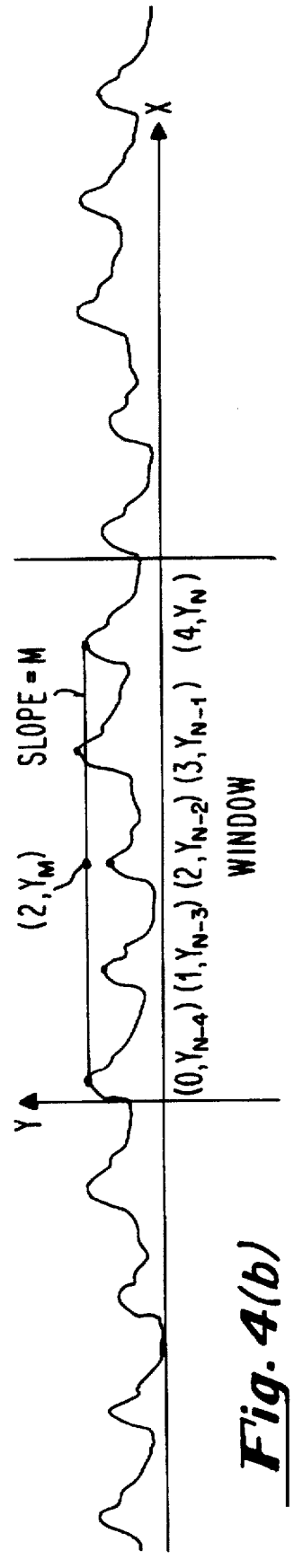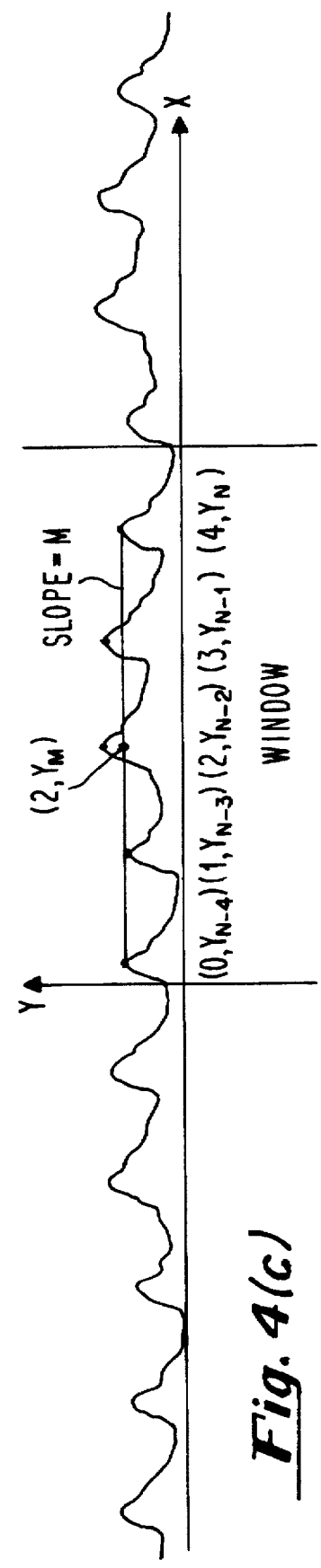

MITIGATION OF RESPIRATORY ARTIFACT IN BLOOD PRESSURE SIGNAL USING LINE SEGMENT SMOOTHING

FIELD OF THE INVENTION

This invention relates to automated blood pressure monitoring, and more particularly, to techniques for processing the blood pressure signals obtained by such automated blood pressure monitors so as to minimize the effects of respiratory artifacts.

BACKGROUND OF THE INVENTION

During operations, a patient's blood pressure is commonly monitored using invasive or noninvasive blood pressure monitors having transducers attached to the patient. Unfortunately, some blood pressure transducer sites on the patient's body present a signal which is considerably affected by artifacts resulting from the mechanics of the breathing of the patient. This artifact generally appears as a low frequency rise and fall as the patient inhales and exhales, respectively. The blood pressure signal is modulated by this rise and fall and is thus superimposed upon a "wandering baseline" type artifact. Since the blood pressure transducer sites which exhibit this artifact also often provide very low magnitude signals, the effect of this artifact may be clinically significant if not removed. The determination of the true blood pressure value in the presence of respiratory artifacts is further complicated by the fact that the increase and decrease effects are reversed when the patient is being mechanically ventilated, as opposed to breathing spontaneously.

The effect of the respiratory artifact has been described in some detail by Ellis in an article entitled "Interpretation of Beat-To-Beat Blood Pressure Values in the Presence of Ventilatory Changes," *Journal of Clinical Monitoring*, Vol. 1, No. 1, January, 1985, pages 65–70. As noted by Ellis, only during the "end expiratory" portion of the blood pressure signal (neither inhaling nor exhaling) is the blood pressure value actually representative of the actual blood pressure, which is, of course, due to the absence of the respiratory artifact. Ellis further describes an algorithm for selecting values that appear physiologically useful from blood pressure waveforms that vary with ventilation. In particular, Ellis proposes to minimize the effects of ventilation on the blood pressure determination by using a "weighted average" method of eliminating the respiratory artifact. In Ellis' method, each heart beat's mean value is compared to the mean value of the previous heart beat, and the relative amount of difference between the two is used as a weighting factor in a moving average. If the difference is small, as at the end expiratory portion, the instantaneous value is weighted heavily into the average, and if the difference is large, as during inhalation, the instantaneous value is weighted lightly into the average. The weighting value can thus change for every heart beat.

Because the heart beats are weighted so that the filtered, displayed value corresponds to the average of end-expiratory heart beats, the simple averaging method disclosed by Ellis may be effective at reducing respiratory artifacts to those present at the end expiratory portion of the ventilation cycle. However, such a technique is limited in that the length of the data buffers and the relative size of the weighting factors are not easily made dynamic enough to compensate for sudden changes in blood pressure.

Other common techniques for minimizing the respiratory artifact, such as averaging a buffer of a number of the previous heart beat values, is also undesirable since it is relatively unresponsive to sudden changes in pressure in that an abrupt and persistent change in pressure needs to ripple all the way through a large averaging buffer before it can be seen.

It is, accordingly, a primary object of the present invention to mitigate the effects of the respiratory artifact in a blood pressure signal by favoring the stable parts of the blood pressure waveform yet providing a technique for active smoothing of the blood pressure waveform. The present invention has been designed for this purpose.

SUMMARY OF THE INVENTION

The above objects have been met in accordance with the present invention by providing a blood pressure monitoring apparatus which reduces the effects of respiration artifacts in the blood pressure samples prior to display by determining, for each heart beat detected in the blood pressure samples, the blood pressure at a median point of a line connecting a systolic, diastolic, or mean value for a current heart beat with a corresponding systolic, diastolic, or mean value for a heart beat N-1 heart beats prior to the current heart beat. The median blood pressure value for the current heart beat is then averaged with the blood pressure values of the median points of, for example, the 2N heart beats immediately previous to the current heart beat, and the resulting average is output to the display as indicative of the systolic, diastolic, or mean pressure for the current heart beat. This process is repeated for each heart beat, as desired, until the systolic, diastolic, and mean pressures are determined for each heart beat.

A preferred embodiment of the blood pressure monitoring apparatus of the invention comprises one or more pressure transducers which sense a patient's blood pressure and output a blood pressure signal, an A/D converter which samples the blood pressure signal and outputs blood pressure samples, a microprocessor which includes software for processing the blood pressure samples to determine blood pressure characteristic values, such as systolic, diastolic, and mean blood pressures, representative of a patient's blood pressure, a display buffer which stores the blood pressure characteristic values for the current heart beat, and a display monitor which displays the blood pressure characteristic values stored in the display buffer as indicative of the patient's blood pressure. In accordance with the invention, the microprocessor includes respiration artifact reduction software which reduces respiratory artifacts in the blood pressure samples by determining, for each heart beat detected in the blood pressure samples, the blood pressure at a median point of a line connecting a blood pressure characteristic value for a current heart beat with a corresponding blood pressure characteristic value for a heart beat N-1 heart beats prior to the current heart beat. The value of the blood pressure of the median point determined by the microprocessor is then stored in the display buffer as the display value for the processed systolic, diastolic, or mean blood pressure value.

Preferably, the respiration artifact reduction software further averages the blood pressure value of the median point for the current heart beat with the blood pressure values of the median points of, for example, 2N heart beats immediately previous to the current heart beat and stores the resulting average in the display buffer as the blood pressure characteristic value (systolic, diastolic, or mean blood pressure value) for the current heart beat. Also, as desired, the apparatus may also include a blood pressure sample averaging device which averages adjacent blood pressure samples prior to application of the blood pressure samples to the microprocessor for processing.

The scope of the invention also includes a method of determining a patient's blood pressure by performing the steps of:

applying at least one transducer to the patient so as to sense the patient's blood pressure and outputting a blood pressure signal;

sampling the blood pressure signal and outputting blood pressure samples;

processing the blood pressure samples to determine blood pressure characteristic values, such as systolic, diastolic, and mean blood pressure values, representative of the patient's blood pressure, the processing step including the steps of detecting the patient's heart beat from the blood pressure samples, reducing respiratory artifacts in the blood pressure samples by determining, for each heart beat detected in the blood pressure samples, the blood pressure at a median point of a line connecting a blood pressure characteristic value for a current heart beat with a corresponding blood pressure characteristic value for a heart beat N-1 heart beats prior to the current heart beat, and storing a value of the blood pressure of the median point as the blood pressure characteristic value for the current heart beat; and displaying the blood pressure characteristic values determined in the processing step as indicative of the patient's blood pressure.

Preferably, the processing step includes the additional steps of averaging the blood pressure value of the median point for the current heart beat with the blood pressure values of the median points of, for example, the 2N heart beats immediately previous to the current heart beat and storing the resulting average as the blood pressure characteristic value for the current heart beat. The processing step also includes the steps of identifying heart beats in the blood pressure samples and determining the systolic, diastolic, and mean pressures for each heart beat. Also, if desired, the method of the invention may also include the step of averaging adjacent blood pressure samples prior to processing in the processing step.

The method of the invention is advantageous in that it favors stable parts of the blood pressure waveform (end expiratory portions) yet actively smooths the variable parts of the blood pressure waveform.

BRIEF DESCRIPTION OF THE DRAWINGS

The present invention will be better understood after reading the following detailed description of the presently preferred embodiments thereof with reference to the appended drawing in which:

FIGS. 4(a)–(4c) together illustrate the technique for determining median point within a moving sample window in accordance with the invention.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 1–4. Those skilled in the art will readily appreciate that the description given herein with respect to those figures is for explanatory purposes only and is not intended in any way to limit the scope of the invention. All questions regarding the scope of the invention should be resolved by referring to the appended claims.

Figure 1:
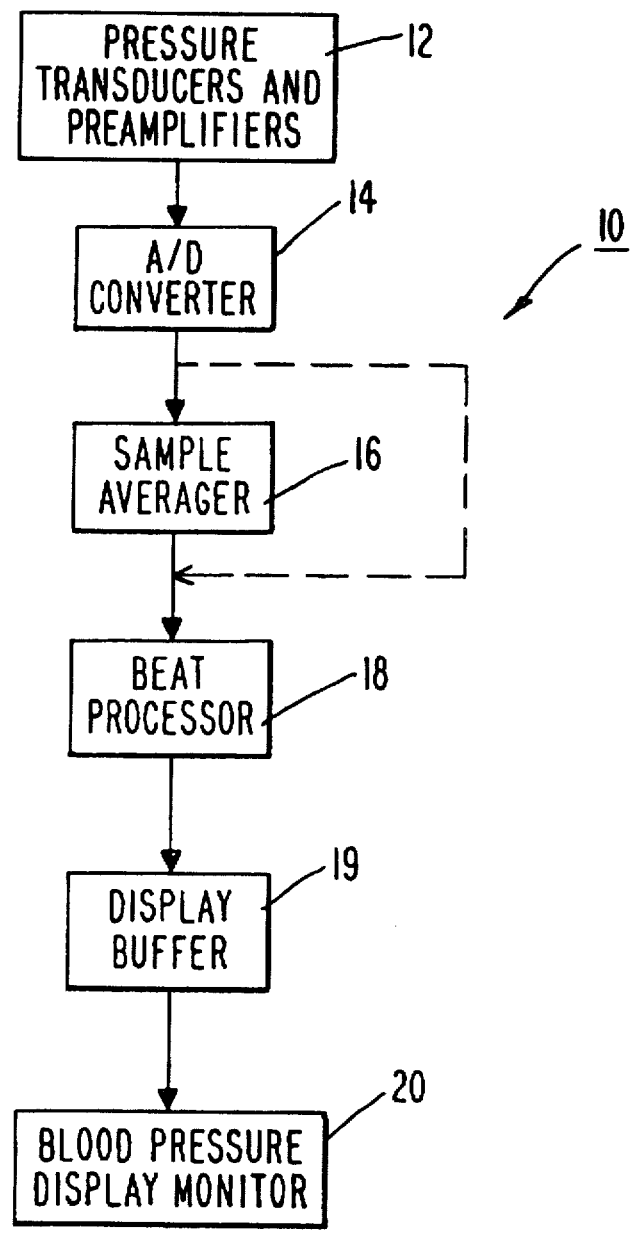
FIG. 1 is a simplified block diagram of a blood pressure monitoring device in accordance with the invention.

A simplified block diagram of a blood pressure monitoring device 10 in accordance with the invention is illustrated in FIG. 1. As shown, blood pressure monitoring device 10 includes one or more standard blood pressure transducers and preamplifiers 12 which provide analog signals representative of the patient's blood pressure in a conventional manner. The blood pressure transducers are typically invasive blood pressure transducers placed on the patient's body or within the patient's bloodstream, although the blood pressure transducers may also be associated with the pneumatic cuff of a noninvasive blood pressure monitoring device. The blood pressure signals provided by blood pressure transducers and preamplifiers 12 are sampled and digitized by an A/D converter 14 in a conventional manner. In a presently preferred embodiment, the blood pressure signals are sampled by A/D converter 14 at 400 Hz to provide 12-bit digital representations of the blood pressure signals at the respective sampling intervals. Then, as desired, every two adjacent samples may be averaged by sample averager 16 so that an effective 200 Hz digital stream representative of the blood pressure signals is provided to the heart beat processor 18 for processing. As will be explained in more detail below, heart beat processor 18 is a microprocessor with application software for processing the blood pressure data to determine, inter alia, the patient's systolic, diastolic, and mean blood pressure for each heart beat. These values are typically stored in a display buffer 19 and provided to a blood pressure display monitor 20 for evaluation by the patient's diagnostician.

Figure 2:
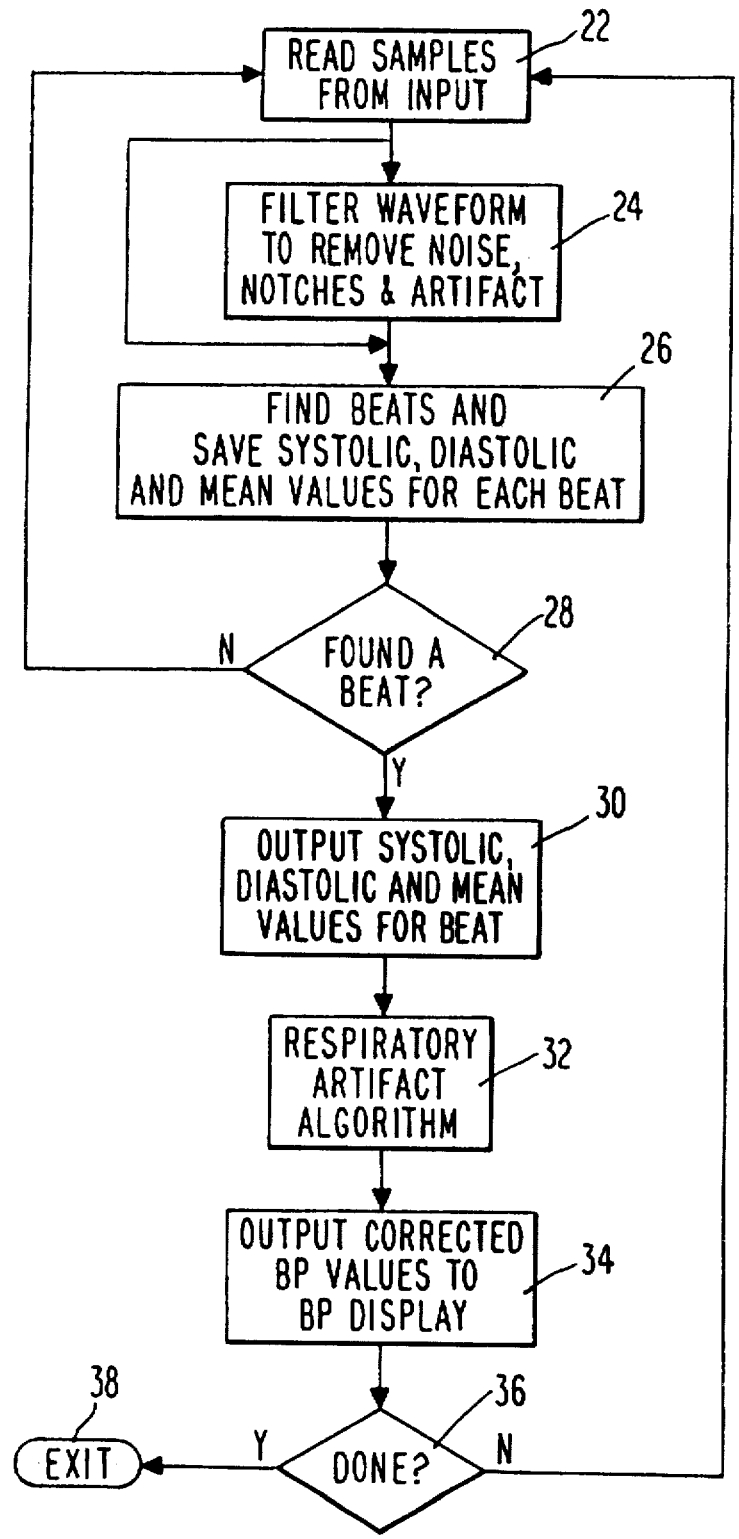
FIG. 2 illustrates the processing performed by heart beat processor 18 of FIG. 1.

FIG. 2 illustrates in simplified form the blood pressure data processing software implemented on heart beat processor 18 of FIG. 1. As illustrated, the blood pressure data samples provided by A/D converter 14 or sample averager 16 are read into the blood pressure data processing software at step 22. The blood pressure waveform data is then filtered at step 24 in a conventional manner to remove noise (spikes), notches, and artifacts caused by patient movement and the like. Then, at step 26, the filtered blood pressure waveform data is processed using conventional threshold methods to find the patient's heart beats. By filtering the blood pressure waveform prior to threshold heart beat detection, the notches and noise are not confused for heart beats. If a heart beat is found, the maximum pressure (systolic), minimum pressure (diastolic), and mean pressure (mean) is determined from the unfiltered (raw data) stream and accumulated for each detected heart beat while the threshold analysis is being performed. However, if no heart beat is found, then at step 28 additional blood pressure samples are read into the blood pressure data processing software. If a heart beat is found, the systolic, diastolic, and mean pressures determined in step 26 are output at step 30 to a respiratory artifact reduction algorithm (FIG. 3) for processing at step 32 in accordance with the techniques of the invention. The corrected data output by the respiratory artifact reduction algorithm of the invention is then outputted to display buffer 19 at step 34 for display on blood pressure display monitor 20. If data processing is completed, the routine is exited at step 38; otherwise, additional blood pressure samples are read in at step 22 and the processing repeated.

Figure 3:
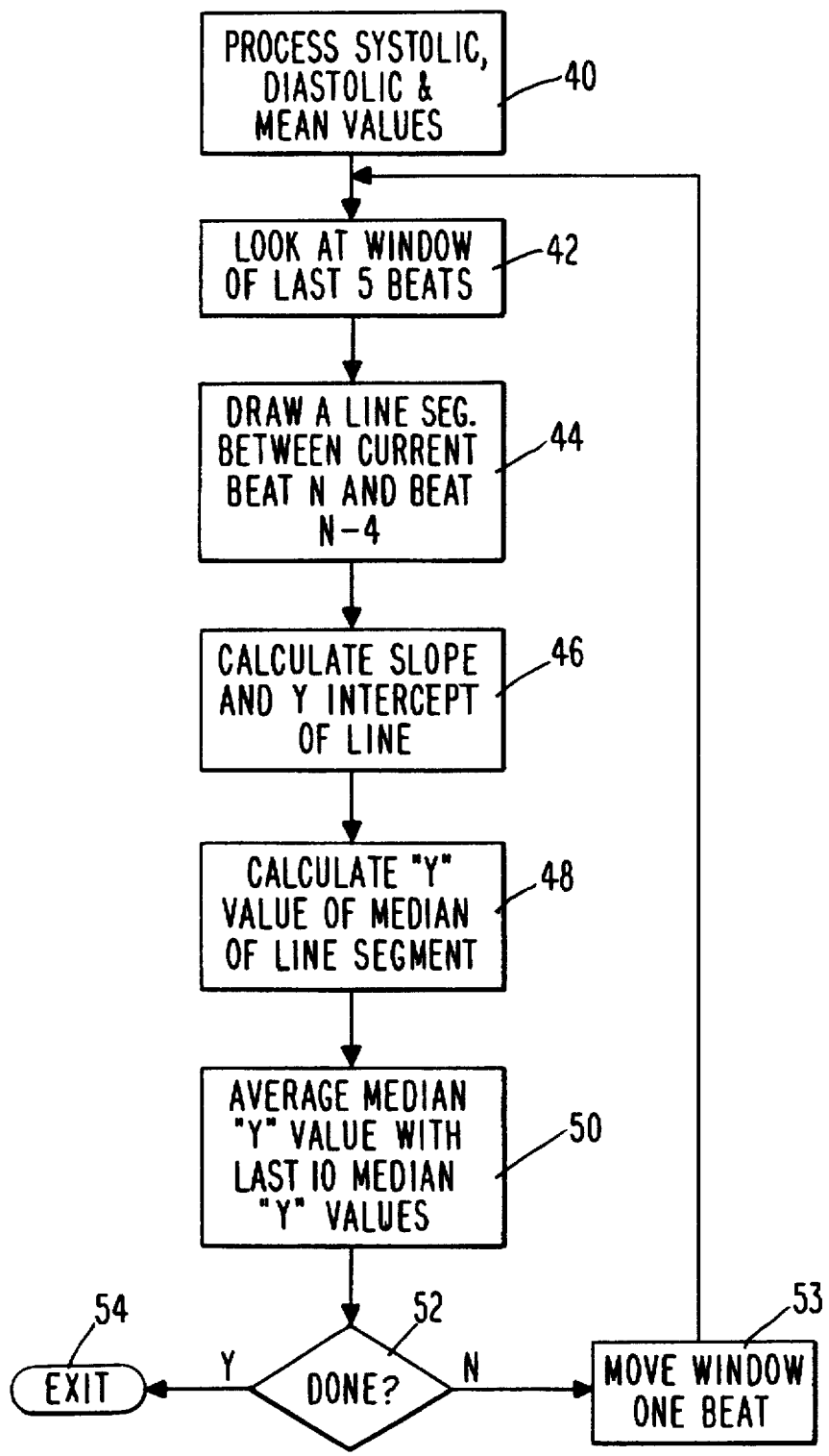
FIG. 3 illustrates a simplified flow chart of the respiratory artifact reduction algorithm in accordance with the invention.

FIG. 3 illustrates a simplified flow chart of the respiratory artifact reduction algorithm in accordance with the invention. The respiratory artifact software in accordance with the invention receives the systolic, diastolic, and mean pressure values from the blood pressure data processing software and, as necessary, processes this data at step 40. Then, at step 42, for each of the three derived blood pressure parameters (systolic, diastolic, and mean pressures), a moving window of a small number (N) of the most recent instantaneous heart beat values is maintained on the parameter data. In the sample embodiment described herein, N is 5, and the heart beats are labeled 0–4, where heart beat 4 is the current heart beat. Of course, N may be any number, and N=5 is chosen based on considerations such as processing power and the like. Next, at step 44, an imaginary line segment is drawn between the end points of what would be the graphical representation of the N heart beat values on a display axis. For example, as illustrated in FIG. 4(a), where the time axis is the x coordinate and the blood pressure value for the parameter is the y axis, each heart beat value is assigned an x value of 0–4, where the corresponding y value is the parameter value for the corresponding heart beat. As shown in FIG. 4(a), a line segment of slope m is drawn across the endpoints (values for x=N and x=N-4) of that portion of the waveform polynomial which describes the instantaneous heart beat parameter values. In the example of FIG. 4, the line segment connects the systolic values, although the same waveform may be used to draw a line segment connecting the diastolic or mean values in accordance with the invention.

At step 46, the slope m (rise over run) and y-intercept of the line segment connecting the parameter values for x=N and x=N-4 are calculated. The processing is quite simple, particularly since the y-intercept may be defined as the instantaneous heart beat parameter value in window position x=N-4 (x=0). Next, at step 48, the "y" (parameter) value for the median x value of the line segment (for N=5 and x=0–4, the median x would be 2) is then calculated according to the equation $y=mx+b=2m+y_{N-4}$, where x=2 and m is calculated in step 46. The resulting median y value is then put into an averaging buffer which, in a preferred embodiment, is at least twice as large as the size of the window. Hence, the averaging buffer contains at least the 2N most recent calculated median values, which, for N=5 in the illustrated embodiment, would be the 10 most recent calculated median values. Then, at step 50, these 2N median values are averaged with the current y median value, and the resulting y median value is outputted to display buffer 19 for display as the current filtered parameter value for the current heart beat. If it is determined at step 52 that additional heart beat data is to be processed, on the next heart beat detection the new heart beat data is read in and the oldest heart beat data is dropped, thereby incrementing the window position by one heart beat at step 53 as respectively shown in FIGS. 4(b) and 4(c). The processing of steps 42–52 is then repeated for the new window of data, and the newly calculated median heart beat value is put into the averaging buffer, dropping the oldest calculated median heart beat value. Each successive heart beat is processed in this manner.

The processing of FIG. 3 may be performed successively for each of the other parameter values (systolic, diastolic, or mean) not already processed during the current heart beat, or, on the other hand, the processing of each of the parameters could be performed in parallel. The respiratory artifact reduction software is then exited at step 54.

Those skilled in the art will appreciate that the filtering method of the invention is more responsive to sudden changes in pressure than a straight average would be. In fact, the values stored in the averaging buffer are directly related to the changes in the waveform, so the waveform follows any true physiological trends in the blood pressure data rather quickly. In addition, the process of the invention smooths out both noise values and the respiratory baseline variations, while further emphasizing and preserving the flat end expiratory portions of the blood pressure waveform.

Those skilled in the art will appreciate that the respiratory artifact reduction technique in accordance with the invention is better than a large moving straight average window on the heart beat values in that it favors the heart beats on the flat portions of the waveform that are unaffected by the artifact, and yet is responsive to true physiological changes in pressure. An abrupt and persistent change in pressure does not need to ripple all the way through a large averaging buffer before it can be seen. Moreover, the technique of the invention eliminates concerns about how to size the averaging buffer relative to the variability of both the breath rate and heart rate, since the median averaging process of the invention does the initial smoothing on the variable part of the response. Since the method of the invention favors the stable parts of the blood pressure waveform while actively smoothing the variable parts of the waveform, it is more responsive than the prior art Ellis method described above.

It will be appreciated by those skilled in the art that the foregoing has set forth the presently preferred embodiment of the invention and an illustrative embodiment of the invention but that numerous alternative embodiments are possible without departing from the novel teachings of the invention. For example, those skilled in the art will appreciate that the techniques of the invention may be used with invasive blood pressure monitors as well as noninvasive blood pressure monitors of the type described, for example, in U.S. Pat. Nos. 4,349,034 and 4,360,029. All such modifications are intended to be included within the scope of the appended claims.

I claim:

1. A blood pressure monitoring apparatus, comprising:
   at least one pressure transducer which senses a patient's blood pressure and outputs a blood pressure signal;
   an A/D converter which samples said blood pressure signal and outputs blood pressure samples;
   a microprocessor which processes said blood pressure samples to determine blood pressure characteristic values representative of a patient's blood pressure, said microprocessor including respiration artifact reduction software which reduces respiratory artifacts in said blood pressure samples by determining, for each heart beat detected in said blood pressure samples, the blood pressure at a median point of a line connecting a blood pressure characteristic value for a current heart beat with a corresponding blood pressure characteristic value for a heart beat a predetermined number of heart beats prior to said current heart beat;
   a display buffer which stores a value of the blood pressure of said median point determined by said microprocessor as the blood pressure characteristic value for the current heart beat; and
   a display monitor which displays the blood pressure characteristic values stored in said display buffer as indicative of the patient's blood pressure.

2. An apparatus as in claim 1, wherein said respiration artifact reduction software further averages the blood pressure value of the median point for the current heart beat with the blood pressure values of the median points of a number of heart beats immediately previous to said current heart beat and stores a resulting average in said display buffer as the blood pressure characteristic value for the current heart beat.

3. An apparatus as in claim 2, wherein said blood pressure characteristic values represent at least one of the systolic blood pressure, diastolic blood pressure, and mean blood pressure for each heart beat of the patient.

4. An apparatus as in claim 3, wherein said respiratory artifact reduction software determines the median points for the systolic blood pressure, diastolic blood pressure, and mean blood pressure for the current heart beat of the patient and stores in said display buffer the respective values of the blood pressures of said median points as respectively indicative of said systolic blood pressure, said diastolic blood pressure, and said mean blood pressure for the current heart beat.

5. An apparatus as in claim 3, wherein said microprocessor further includes heart beat detection software which identifies heart beats in said blood pressure samples and determines the systolic, diastolic, and mean pressures for each heart beat.

6. An apparatus as in claim 1, further comprising a blood pressure sample averaging device which averages adjacent blood pressure samples prior to application of said blood pressure samples to said microprocessor for processing.

7. A blood pressure monitoring apparatus, comprising:

means for sensing a patient's blood pressure and outputting a blood pressure signal;

means for sampling said blood pressure signal and outputting blood pressure samples;

means for processing said blood pressure samples to determine blood pressure characteristic values representative of a patient's blood pressure, said processing means including means for reducing respiratory artifacts in said blood pressure samples by determining, for each heart beat detected in said blood pressure samples, the blood pressure at a median point of a line connecting a blood pressure characteristic value for a current heart beat with a corresponding blood pressure characteristic value for a heart beat a predetermined number of heart beats prior to said current heart beat, and for storing a value of the blood pressure of said median point as the blood pressure characteristic value for the current heart beat; and display means for displaying the blood pressure characteristic values determined by said processing means as indicative of the patient's blood pressure.

8. An apparatus as in claim 7, wherein said processing means further comprises means for averaging the blood pressure value of the median point for the current heart beat with the blood pressure values of the median points of a number of heart beats immediately previous to said current heart beat and for storing a resulting average as the blood pressure characteristic value for the current heart beat.

9. An apparatus as in claim 8, wherein said blood pressure characteristic values represent at least one of the systolic blood pressure, diastolic blood pressure, and mean blood pressure for each heart beat of the patient.

10. An apparatus as in claim 9, wherein said processing means includes means for determining the median points for the systolic blood pressure, diastolic blood pressure, and mean blood pressure for the current heart beat of the patient and for storing the respective values of the blood pressures of said median points as respectively indicative of said systolic blood pressure, said diastolic blood pressure, and said mean blood pressure for the current heart beat.

11. An apparatus as in claim 9, wherein said processing means further includes means for identifying heart beats in said blood pressure samples and for determining the systolic, diastolic, and mean pressures for each heart beat.

12. An apparatus as in claim 7, further comprising averaging means for averaging adjacent blood pressure samples prior to application of said blood pressure samples to said processing means for processing.

13. A method of determining a patient's blood pressure, comprising the steps of:

applying at least one transducer to the patient so as to sense the patient's blood pressure and outputting a blood pressure signal;

sampling the blood pressure signal and outputting blood pressure samples;

processing the blood pressure samples to determine blood pressure characteristic values representative of the patient's blood pressure, said processing step including the steps of detecting the patient's heart beat from said blood pressure samples, reducing respiratory artifacts in said blood pressure samples by determining, for each heart beat detected in said blood pressure samples, the blood pressure at a median point of a line connecting a blood pressure characteristic value for a current heart beat with a corresponding blood pressure characteristic value for a heart beat a predetermined number of heart beats prior to said current heart beat, and storing a value of the blood pressure of said median point as the blood pressure characteristic value for the current heart beat; and displaying the blood pressure characteristic values determined in said processing step as indicative of the patient's blood pressure.

14. A method as in claim 13, wherein said processing step includes the additional steps of averaging the blood pressure value of the median point for the current heart beat with the blood pressure values of the median points of a number of heart beats immediately previous to said current heart beat and storing a resulting average as the blood pressure characteristic value for the current heart beat.

15. A method as in claim 14, wherein said blood pressure characteristic values represent at least one of the systolic blood pressure, diastolic blood pressure, and mean blood pressure for each heart beat of the patient.

16. A method as in claim 15, wherein said processing step includes the steps of determining the median points for the systolic blood pressure, diastolic blood pressure, and mean blood pressure for the current heart beat of the patient and storing the respective values of the blood pressures of said median points as respectively indicative of said systolic blood pressure, said diastolic blood pressure, and said mean blood pressure for the current heart beat.

17. A method as in claim 15, wherein said processing step includes the steps of identifying heart beats in said blood pressure samples and determining the systolic, diastolic, and mean pressures for each heart beat.

18. An apparatus as in claim 13, further comprising the step of averaging adjacent blood pressure samples prior to processing in said processing step.

* * * * *